(12) United States Patent
Asakawa

(10) Patent No.: US 8,332,157 B2
(45) Date of Patent: Dec. 11, 2012

(54) INFORMATION PROCESSING APPARATUS, INFORMATION PROCESSING METHOD, AND PROGRAM

(75) Inventor: Takeshi Asakawa, Chiba (JP)

(73) Assignee: Sony Corporation, Tokyo (JP)

( * ) Notice: Subject to any disclaimer, the term of this patent is extended or adjusted under 35 U.S.C. 154(b) by 73 days.

(21) Appl. No.: 13/082,950

(22) Filed: Apr. 8, 2011

(65) Prior Publication Data

US 2011/0282638 A1 Nov. 17, 2011

(30) Foreign Application Priority Data

May 11, 2010 (JP) ................................. 2010-109644

(51) Int. Cl.
*G06F 19/00* (2011.01)
*G11C 17/00* (2006.01)

(52) U.S. Cl. ................................. 702/19; 365/94; 700/1

(58) Field of Classification Search ........................ None
See application file for complete search history.

(56) References Cited

U.S. PATENT DOCUMENTS

| 5,163,426 A | 11/1992 | Czeisler et al. |
| 5,167,228 A | 12/1992 | Czeisler et al. |

FOREIGN PATENT DOCUMENTS

| JP | 2-503875 | 11/1990 |
| JP | 4-506020 | 10/1992 |

OTHER PUBLICATIONS

Gander et al. Phase shifting two coupled circadian pacemakers: implications for jet lag American Journal of Physiology vol. 249, pp. R 704-R719(1985).*

AJ Davidson et al, "Fatal effects of an immune challenge following repeated phase shifts," XI. Congress of the European Biological Rhythms Society (EBRS2009), Symposium 19. Hot topics S19-1, 2009, p. 102.

Mamoru Nagano et al., "An Abrupt Shift in the Day/Night Cycle Causes Desynchrony in the Mammalian Circadian Center," The Journal of Neuroscience, Jul. 9, 2003, pp. 6141-6151.

Takeshi Asakawa et al., "Mathematical model for describing suprachiasmatic nucleus at Jet lag," Second Japanese society for quantitative biology, 2010, 1 page.

Albert Goldbeter, "A model for circadian oscillations in the *Drosophila* period protein (PER)," The Royal Society, B261, 1995, pp. 319-324.

* cited by examiner

*Primary Examiner* — John S Brusca
(74) *Attorney, Agent, or Firm* — Oblon, Spivak, McClelland, Maier & Neustadt, L.L.P.

(57) ABSTRACT

An information processing apparatus includes: an acquisition mechanism acquiring information on biological time of a user and information on a time difference between a movement source of the user and a movement destination; a storage mechanism storing model information produced by modeling a sunshine pattern, an expression pattern of a clock gene of a neuron of a ventrolateral area of a suprachiasmatic nucleus, and an expression pattern of a clock gene of a neuron of a dorsomedial area; and when a sunshine pattern of the movement source is changed in accordance with the time difference so as to become a sunshine pattern of the movement destination, a simulation mechanism simulating the expression pattern of the ventrolateral area and the expression pattern of the dorsomedial area on the basis of the model information using a state identified by the biological time as a starting state.

7 Claims, 9 Drawing Sheets

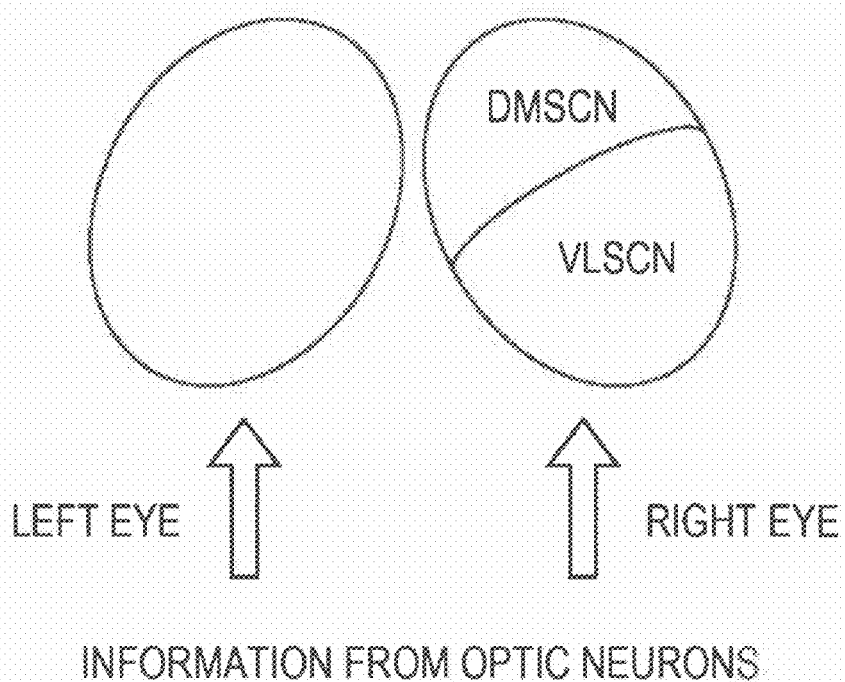

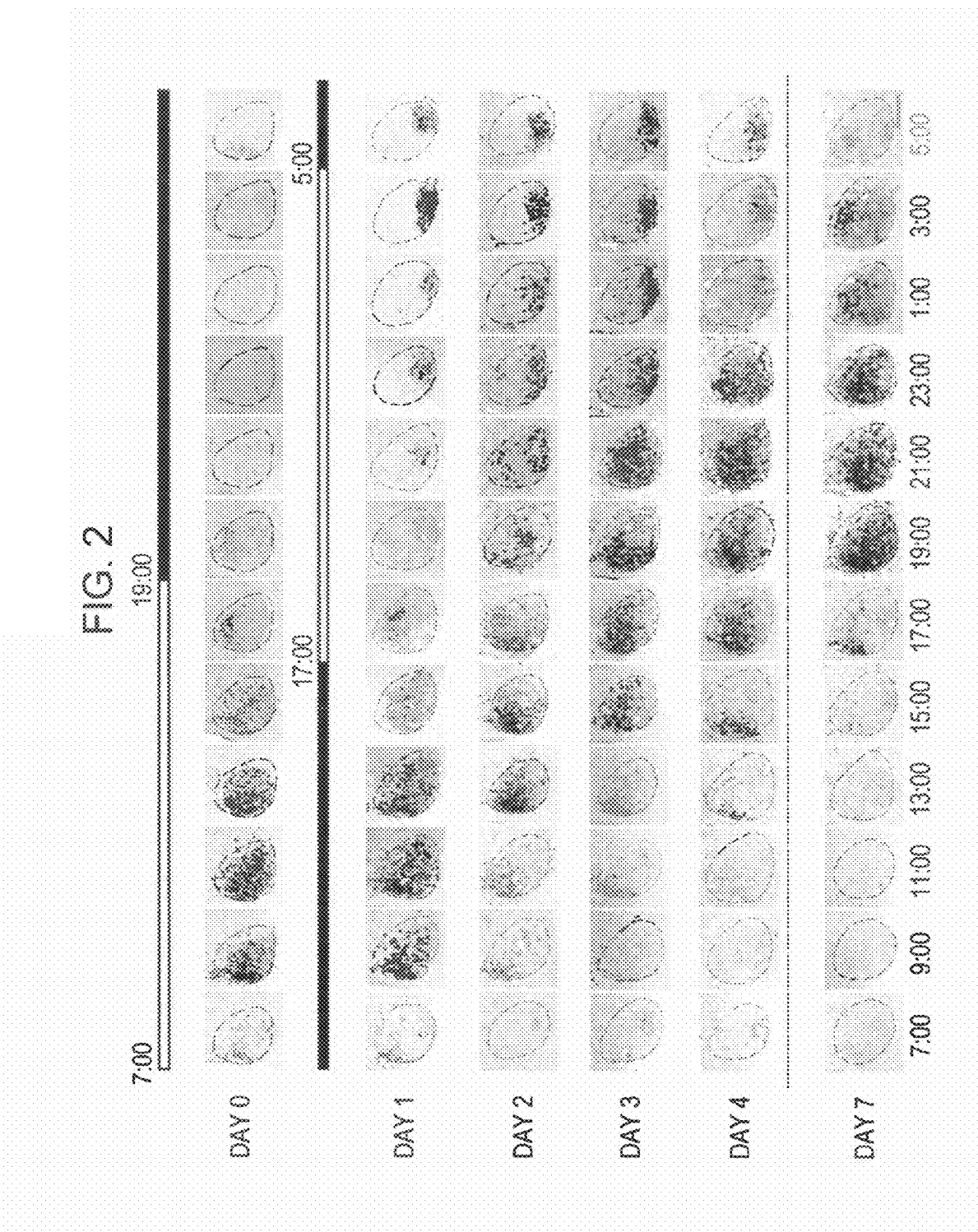

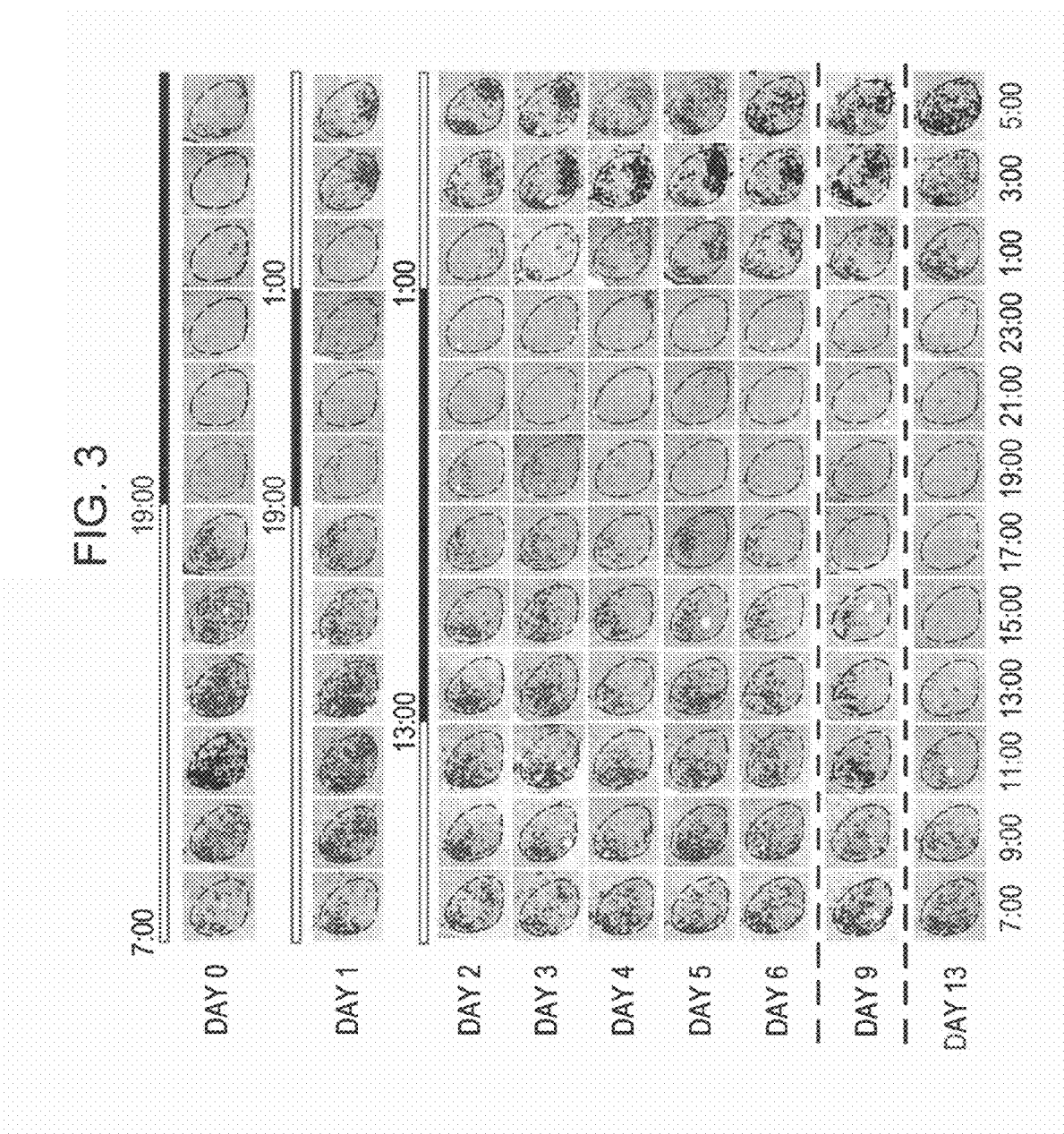

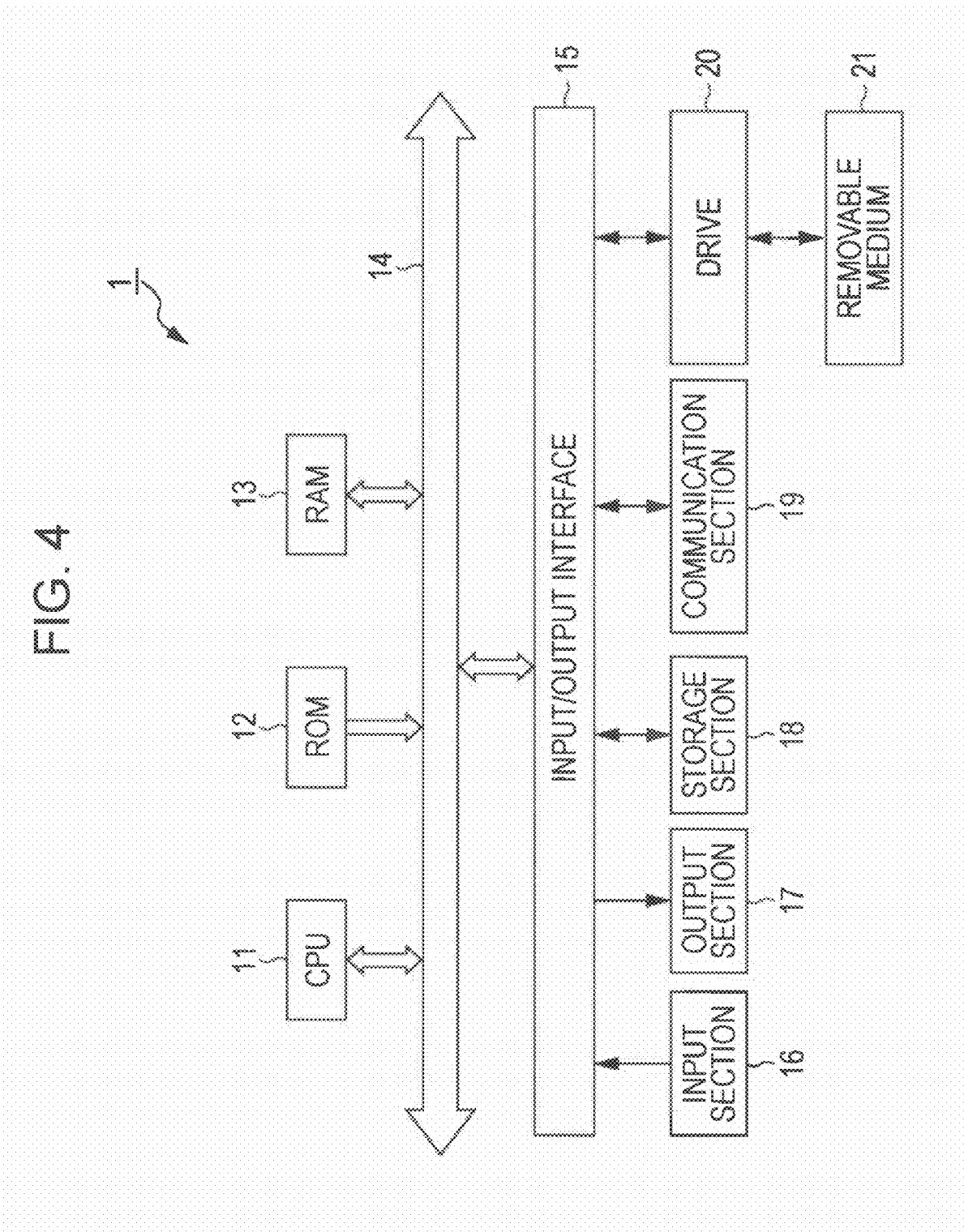

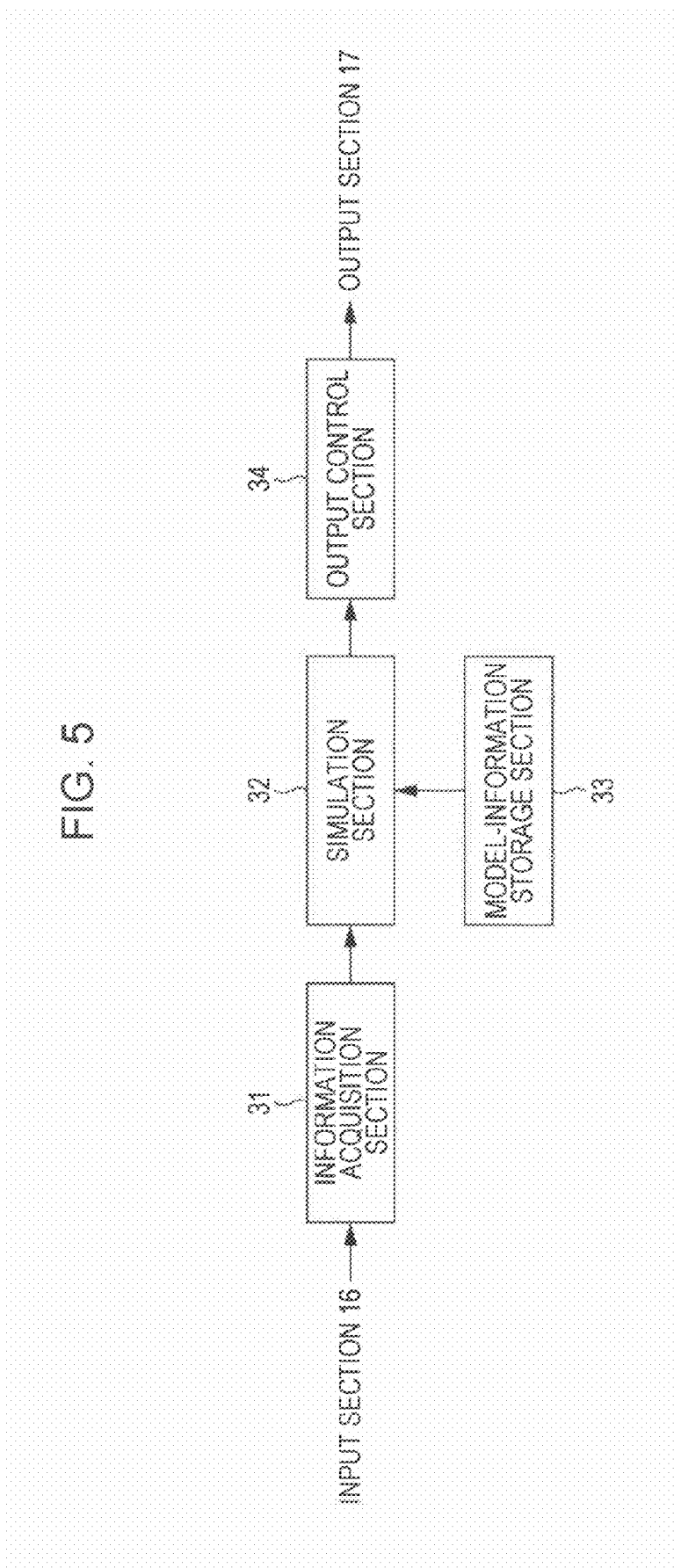

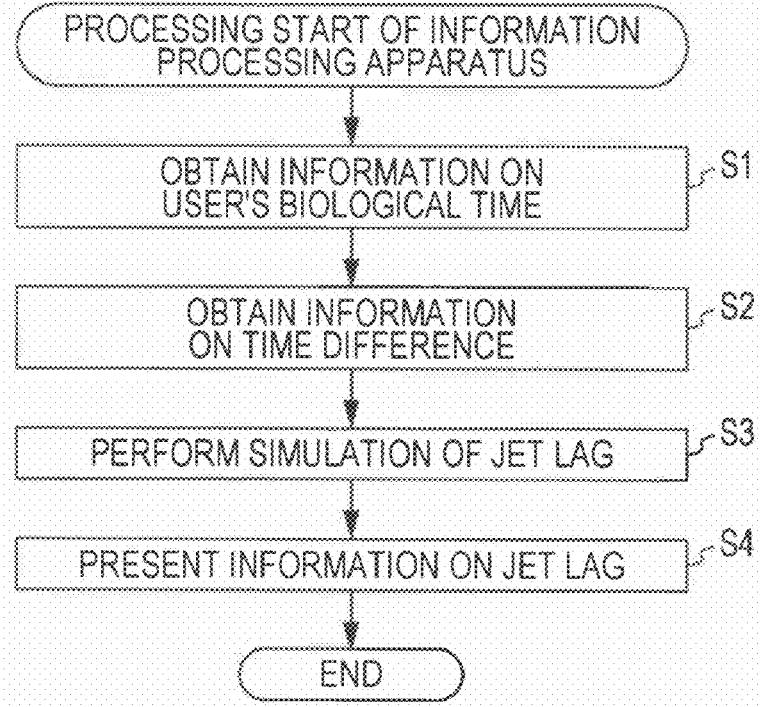
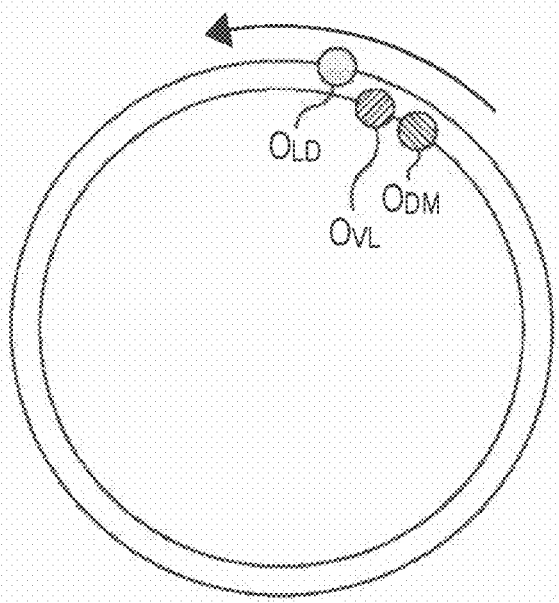

INFORMATION PROCESSING APPARATUS, INFORMATION PROCESSING METHOD, AND PROGRAM

BACKGROUND OF THE INVENTION

1. Field of the Invention

The present invention relates to an information processing apparatus, an information processing method, and a program. In particular, the present invention relates to an information processing apparatus, an information processing method, and a program that enables each user to predict a state of his or her jet-lag syndrome more easily.

2. Description of the Related Art

Since mankind has obtained an aircraft, which is a means of transportation, a phenomenon called jet-lag syndrome (hereinafter, suitably called "jet lag") has become a big issue. It is unlikely that light-irradiation time suddenly changes as an external environment in nature, and thus jet lag is said to be a phenomenon that has not been experienced by human beings from the viewpoint of biological evolution.

In recent years, there has been a report on a phenomenon in which when an aged rat had suffered from jet lag by suddenly changing light irradiation time, a sudden death occurred in that rat (Lecture material at XI. Congress of the European biological Rhythms Society (EBRS2009), "Symposium 19. Hot topics" S19-1 "Fatal Effects of an immune challenge following repeated phase shifts", Davidson A J, Castanon-Cervantes O, Ehlen C, Menaker M, Paul K). The same thing might occur to a human being, and thus investigation is urged on what action of jet lag causes death of an individual.

Also, in recent years, researches have revealed that jet lag is a phenomenon that occurs during a period from time when synchronization of expressions of clock genes in a nerve center called a suprachiasmatic nucleus in a brain, which is a central clock of a mammal, is temporarily lost (split into two kinds of synchronization), and to time when the synchronization is obtained again ("An Abrupt Shift in the Day/Night Cycle Causes Desynchrony in the Mammalian Circadian Center", Mamoru Nagano, Akihito Adachi, Ken-ichi Nakahama, Toru Nakamura, Masako Tamada, Elizabeth Meyer-Bernstein, Amita Sehgal, and Yasufumi Shigeyoshi, The Journal of Neuroscience, Jul. 9, 2003•23(14): 6141-6151•6141).

FIG. 1 is a diagram illustrating right and left suprachiasmatic nuclei.

A suprachiasmatic nucleus (SCN) is a set of neurons situated in a hypothalamus in a brain. From anatomical viewpoint, the suprachiasmatic nucleus is roughly divided into a part having photoreceptors receiving light information from optic neurons and a part not having photoreceptors. The former, the part having photoreceptors, is called a ventrolateral area (Ventrolateral SCN (VLSCN)), and the latter, the part not having photoreceptors, is called a dorsomedial area (Dorsomedial SCN (DMSCN)).

In the case of not having jet lag, both of the expression cycles of the clock genes of the VLSCN neurons and of the clock genes of the DMSCN neurons are kept to be 24 hours in synchronism with a sunshine cycle.

When light irradiation time is suddenly changed in this state, it is observed that the VLSCN clock gene immediately follows a change in the light irradiation time, and the expression of the gene is synchronized with the sunshine cycle after the change (light irradiation cycle). However, in the DMSCN clock gene, the expression is not observed to be in synchronization so quickly as the VLSCN clock gene. As a result, desynchronization occurs between oscillation generated by the VLSCN clock gene and oscillation generated by the DMSCN clock gene.

FIG. 2 is a diagram illustrating observation results of expressions of clock genes of neurons included in a suprachiasmatic nucleus of a rat, a model animal, using a method called "in situ hybridization" by taking a typical clock gene PER1 as an example.

FIG. 2 shows observation results in the case of assuming a flight to the west and delaying a sunshine duration by 10 hours. The horizontal axis shows time, and the vertical axis the number of days. Individual states of suprachiasmatic nucleus show states of expressions for individual two hours. A tinted portion in the suprachiasmatic nucleus is a portion of neurons with expressions of the clock genes.

As shown in a highest row, at 0th day (Day0), the expression is observed while light is irradiated. The expression cycle of the clock gene of the VLSCN neurons and the expression cycle of the clock gene of the DMSCN neurons are synchronized with light irradiation cycle. At the 0-day, light is irradiated from 7 o'clock to 19 o'clock.

As shown in a second row, light is not irradiated from 19 o'clock on the 0th day to 17 o'clock on the first day (Day1) so that the sunshine duration is delayed by 10 hours. Light is irradiated from 17 o'clock on the first day to 5 o'clock. After 5 o'clock on the first day, a state with light irradiation and a state without light irradiation are repeated on a 12-hour cycle.

In this case, for example, as is apparent by the observation results at 23 o'clock on the first day, the expression of the clock genes in VLSCN is observed, whereas the expression is not observed in DMSCN. That is to say, desynchronization occurs between VLSCN and DMSCN. As described above, if light irradiation time is suddenly changed, the expression is observed by immediately following the change in light irradiation time in VLSCN having photoreceptors. However, the expression is not observed in DMSCN having no photoreceptors.

The desynchronized state continues until the 6th day. As shown at a lowest row, on the 7th day, resynchronization occurs between the expression cycle of the clock genes in VLSCN and the expression cycle of the clock genes in DMSCN. On 7th day, the expressions of the clock genes in both VLSCN and DMSCN are observed substantially in synchronism with the light irradiation time.

In the case of assuming a flight to the west and delaying sunshine duration by 10 hours, the expressions of the genes responded to the change in sunshine duration on the 7th day. That is to say, jet lag occurred from the first day to the sixth day.

FIG. 3 is a diagram illustrating observation results of the expression in suprachiasmatic nucleus in the case of assuming a flight to the east and advancing sunshine duration by 6 hours.

As shown in a second row in FIG. 3, light starts to be irradiated from 1 o'clock on the 1st day, and thus light irradiation time is advanced by 6 hours.

In this case, for example, as is apparent by the observation results at 3 o'clock on the first day, the expression of the clock genes in VLSCN is observed, whereas the expression is not observed in DMSCN. Thus, desynchronization occurs between VLSCN and DMSCN. The desynchronized state continues until the 12th day. As shown at a lowest row, on the 13th day, resynchronization occurs between the expression cycle of the clock genes in VLSCN and the expression cycle of the clock genes in DMSCN.

As shown in FIG. 3, in the case of assuming a flight to the east and advancing sunshine duration by 6 hours, the expressions of the genes responded to the change in sunshine duration on the 13th day. That is to say, jet lag occurred from the first day to the twelfth day.

As experienced by overseas travel, recovery time from jet lag is different in the case of a flight to the west (in the case of delaying time) and in the case of a flight to the east (in the case of advancing time). Actually, this phenomenon quite matches the period from time when desynchronization occurs between the above-described clock genes in a suprachiasmatic nucleus to time when resynchronization occurs. The observation results like this is described in the non-patent document, "An Abrupt Shift in the Day/Night Cycle Causes Desynchrony in the Mammalian Circadian Center", Mamoru Nagano, Akihito Adachi, Ken-ichi Nakahama, Toru Nakamura, Masako Tamada, Elizabeth Meyer-Bernstein, Amita Sehgal, and Yasufumi Shigeyoshi, The Journal of Neuroscience, Jul. 9, 2003•23(14):6141-6151•6141).

It has been revealed that jet lag is a phenomenon that occurs during an unstable period from time when desynchronization occurs between the expressions of two different kinds of clock genes in a suprachiasmatic nucleus to time when resynchronization occurs. However, it has not been figured out why time periods necessary for resynchronization are different between the case of advancing time and the case of delaying time.

A study is made for modeling in a non-patent document, "Mathematical model expressing SCN at the time of jet lag", Takeshi Asakawa, Satoshi Koinuma, Mamoru Nagano, and Yasufumi Shigeyoshi, poster presentation "Second Japanese society for quantitative biology 2010", as follows. A VLSCN neuron and a DMSCN neuron are expressed as oscillators that are mutually in cooperation with each other, and the clock genes of the VLSCN and DMSCN neuron groups are interpreted as a dissipative system in order to model the system. It is noted that the cause for one neuron in a suprachiasmatic nucleus producing limit-cycle oscillation is the fact that a clock-gene network itself constitutes a negative feedback loop (refer to "A model for circadian oscillation in the Drosophila period protein (PER)", Goldbeter A., Proc. R. Soc. London Ser. B261, 391-324).

SUMMARY OF THE INVENTION

It is important to effectively cure jet lag for health and for social activities. If it is possible to reproduce the process from desynchronization of the two kinds of oscillators in a suprachiasmatic nucleus, which is the cause of jet lag, to the resynchronization thereof by computer simulation, it becomes possible to understand how the biological clocks go out of order, and then return to a former state.

In the mathematical model studied in the non-patent document, "Mathematical model expressing SCN at the time of jet lag", Takeshi Asakawa, Satoshi Koinuma, Mamoru Nagano, and Yasufumi Shigeyoshi, poster presentation "Second Japanese society for quantitative biology 2010", one VLSCN neuron and one DMSCN neuron are represented, but the model is very complicated. Even a mathematical description on one neuron is sufficiently complicated. For practical applications, VLSCN and DMSCN are individual sets of neurons, and thus it is necessary to simulate a multiple-body connection system. However, the model is not suitable for such a case.

The present invention has been made in view of these circumstances. It is desirable to allow each user to predict a state of his or her jet-lag syndrome more easily.

According to an embodiment of the present invention, there is provided an information processing apparatus including: an acquisition means for acquiring information on biological time of a user and information on a time difference between a movement source of the user and a movement destination; a storage means for storing model information produced by modeling a sunshine pattern, an expression pattern of a clock gene of a neuron of a ventrolateral area of a suprachiasmatic nucleus, and an expression pattern of a clock gene of a neuron of a dorsomedial area; and when a sunshine pattern of the movement source is changed in accordance with the time difference so as to become a sunshine pattern of the movement destination of the user, a simulation means for simulating the expression pattern of the clock gene of the neuron of the ventrolateral area and the expression pattern of the clock gene of the neuron of the dorsomedial area on the basis of the model information using a state identified by the biological time of the user as a starting state.

The information processing apparatus may further include an output means for outputting information on a predicted jet-lag syndrome occurring on the user on the basis of a simulation result by the simulation means.

The output means may display a time period during which desynchronization occurs between the expression pattern of the clock gene of the neuron of the ventrolateral area and the expression pattern of the clock gene of the neuron of the dorsomedial area.

The output means may display an image indicating the expression pattern of the clock gene of the neuron of the ventrolateral area and the expression pattern of the clock gene of the neuron of the dorsomedial area from time when desynchronization occurs to time when re-synchronization is established.

According to another embodiment of the present invention, there is provided a method of processing information, including the steps of: acquiring information on biological time of a user and information on a time difference of a movement destination of the user; and when a sunshine pattern of a movement source of the user is changed in accordance with the time difference so as to become a sunshine pattern of the movement destination of the user, simulating an expression pattern of a clock gene of a neuron of a ventrolateral area of the suprachiasmatic nucleus and an expression pattern of a clock gene of a neuron of a dorsomedial area on the basis of model information stored in a storage means and produced by modeling a sunshine pattern, an expression pattern of a clock gene of a neuron of a ventrolateral area of a suprachiasmatic nucleus, and an expression pattern of a clock gene of a neuron of a dorsomedial area using a state identified by the biological time of the user as a starting state.

According to another embodiment of the present invention, there is provided a program for causing a computer to perform processing including the steps of: acquiring information on biological time of a user and information on a time difference of a movement destination of the user; and when a sunshine pattern of a movement source of the user is changed in accordance with the time difference so as to become a sunshine pattern of the movement destination of the user, simulating an expression pattern of a clock gene of a neuron of a ventrolateral area of the suprachiasmatic nucleus and an expression pattern of a clock gene of a neuron of a dorsomedial area on the basis of model information stored in a storage means and produced by modeling a sunshine pattern, an expression pattern of a clock gene of a neuron of a ventrolateral area of a suprachiasmatic nucleus, and an expression pattern of a clock gene of a neuron of a dorsomedial area using a state identified by the biological time of the user as a starting state.

By an embodiment of the present invention, information on biological time of a user and information on a time difference between a movement source of the user and a movement destination are obtained. And when a sunshine pattern of a movement source is changed in accordance with the time difference so as to become a sunshine pattern of the movement destination of the user, simulating is performed on an expression pattern of a clock gene of a neuron of a ventrolateral area of a suprachiasmatic nucleus and an expression pattern of a clock gene of a neuron of a dorsomedial area using a state identified by the biological time of the user as a starting state.

By the present invention, it is possible for each user to predict a state of his or her jet-lag syndrome more easily.

BRIEF DESCRIPTION OF THE DRAWINGS

FIG. 1 is a diagram illustrating suprachiasmatic nuclei;
FIG. 2 is a diagram illustrating observation results of expressions of clock genes of neurons included in the suprachiasmatic nucleus;
FIG. 3 is a diagram illustrating other observation results of expressions of clock genes of neurons included in the suprachiasmatic nucleus;
FIG. 4 is a block diagram illustrating an example of a configuration of an information processing apparatus according to an embodiment of the present invention;
FIG. 5 is a block diagram illustrating an example of a functional configuration of the information processing apparatus;
FIG. 6 is a flowchart illustrating processing of the information processing apparatus;
FIG. 7 is a diagram illustrating an example of simulation.

DESCRIPTION OF THE PREFERRED EMBODIMENTS

Configuration of Information Processing Apparatus

Figure 8:
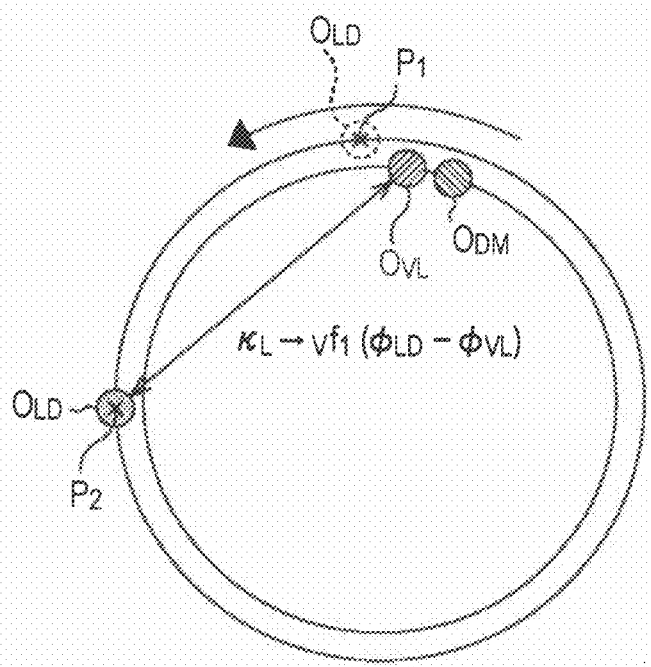
FIG. 8 is a diagram illustrating an example of simulation when time is advanced.

FIG. 4 is a block diagram illustrating an example of a configuration of an information processing apparatus according to an embodiment of the present invention.

An information processing apparatus 1 is an apparatus, such as a personal computer, etc. A CPU (Central Processing Unit) 11, a ROM (Read Only Memory) 12, and a RAM (Random Access Memory) 13 are mutually connected through a bus 14.

Further, an input/output interface 15 is connected to the bus 14. An input section 16 including a keyboard, a mouse, etc., and an output section 17 including a display, a speaker, etc., are connected to the input/output interface 15. Also, a storage section 18 including a hard disk, a nonvolatile memory, etc., a communication section 19 including a network interface, etc., and a drive 20 for driving a removable medium 21, are connected to the input/output interface 15.

In the information processing apparatus 1 having the configuration as described above, the CPU 11 loads programs stored in the storage section 18, etc., to the RAM 13 through the input/output interface 15 and the bus 14 to execute the programs, thereby predetermined processing is performed.

For example, jet-lag simulation is performed in accordance with input by a user, and information on predicted jet lag on the user is presented to the user to be simulated. For the information on the jet lag, a time period during which the jet lag occurs, a time period until jet lag is cured, a recovery date and time from the jet lag, etc., are presented.

Thereby, if the user performs simulation on jet lag, for example before a flight, the user is allowed to grasp the situation of predicted jet lag occurring on the user. Also, it is possible for the user to take action in accordance with the jet-lag situation such that the jet lag continues for a certain period, and thus the user takes a rest during that period, etc.

FIG. 5 is a block diagram illustrating an example of a functional configuration of the information processing apparatus 1.

Among the functional sections shown in FIG. 5, at least a part of them can be achieved by the CPU 11 in FIG. 4 performing predetermined programs. As shown in FIG. 5, in the information processing apparatus 1, an information acquisition section 31, a simulation section 32, a model-information storage section 33, and an output control section 34 are achieved. The information acquisition section 31 is supplied with a signal indicating operation contents performed by the user who is subjected to jet-lag simulation using the input section 16.

The information acquisition section 31 obtains information on a time difference between a movement source and a movement destination on the basis of the signal supplied from the input section 16. The time difference also includes information of whether time is advanced or delayed.

For example, when the user selects a movement source and a movement destination from a world map displayed on the display, the information acquisition section 31 obtains the time difference from the selected movement destination. When the current position of the information processing apparatus 1 is stored in the information acquisition section 31 in advance, or is detected by a GPS (Global Positioning System), it is possible not to select the movement source.

Also, the information acquisition section 31 obtains information on biological time of the user. It is noted that the cycle of a biological clock of a human being is about 25 hours. The information acquisition section 31 obtains information indicating what time it is now by the user's biological time from a human biological clock (hour).

A method of measuring biological time is provided by a certain given way. Information on the biological time measured by that given way is input into the information processing apparatus 1 by operation on the input section 16. The removable medium 21 on which biological time information is recorded may be attached to the information processing apparatus 1, and the biological time information may be obtained by reading the removable medium 21.

For a related-art method of measuring biological time, there are a non-invasive method and an invasive method. The former method includes a method of measuring a core-body temperature for 24 hours, etc. The latter method includes a method of measuring hair root genes, a method of measuring blood pressure for 24 hours, a method of measuring changes of melatonin in blood for 24 hours, etc. Before the user instructs the information processing apparatus 1 to carry out jet-lag simulation, it is necessary for the user to measure the user's biological time, and to input the measurement results into the information processing apparatus 1.

The information acquisition section 31 outputs the information on the time difference and the information on the user's biological time to the simulation section 32.

The simulation section 32 performs jet-lag simulation on the basis of the information supplied from the information acquisition section 31 and model information stored in the model-information storage section 33. The model-information storage section 33 stores information produced as a mathematical model by modeling a sunshine pattern, an expression pattern by a clock gene in a VLSCN neuron of a suprachiasmatic nucleus (circadian-rhythm pattern generated by the expression of a clock gene), and an expression pattern of a clock gene in a DMSCN neuron.

In the jet-lag simulation, the expression pattern of clock genes in the VLSCN neurons and the expression pattern of clock genes in the DMSCN neurons are predicted when the sunshine pattern of the current position, which is the movement source, is changed to the sunshine pattern of the movement destination in accordance with the time difference input by the user. The expression states of the clock genes in the VLSCN and the DMSCN neurons at the time of starting simulation are identified by the biological time input by the user.

Although a detailed description will be given later, in the simulation section 32, jet-lag simulation is performed using phase equations expressed by contracting simultaneous differential equations that express the expression patterns of the individual neurons in the suprachiasmatic nucleus, as described above in the "Mathematical model expressing SCN at the time of jet lag".

Thereby, it is possible to remarkably improve the simulation speed, and to easily perform simulation in consideration of multicellular linkage. It also becomes possible to improve precision of the simulation in consideration of multicellular linkage.

The simulation section 32 outputs information indicating results of the jet-lag simulation to the output control section 34.

When the output control section 34 presents information on the jet lag by displaying on the display, the output control section 34 displays a time period during which the jet lag occurs, a time period until the jet lag is cured, etc., to the display included in the output section 17 on the basis of the information supplied from the simulation section 32.

Also, when the output control section 34 presents information on the jet lag by sound, the output control section 34 outputs sound for notifying a time period during which the jet lag occurs, a time period until the jet lag is cured, etc., from the speaker on the basis of the information supplied from the simulation section 32.

Operation of Information Processing Apparatus

Here, a description will be given of processing of the information processing apparatus 1 with reference to a flowchart in FIG. 6.

In step S1, the information acquisition section 31 obtains information on the biological time of a user to be a target of jet-lag simulation.

In step S2, the information acquisition section 31 obtains information on a time difference between the current position of the user and a movement destination.

In step S3, the simulation section 32 performs jet-lag simulation on the basis of the information obtained by the information acquisition section 31 and the model information stored in the model-information storage section 33.

In step S4, the model-information storage section 33 presents information on the jet lag to the user by displaying on the display or by outputting sound from the speaker on the basis of the simulation results by the simulation section 32. After that, the processing is terminated.

Jet-lag Simulation

Here, a detailed description will be given of the jet-lag simulation performed in the simulation section 32.

In the model information used for simulation, a cycle of external day/night, and VLSCN and DMSCN of a suprachiasmatic nucleus are individually expressed as oscillators.

For example, it is assumed that a phase of the oscillator (LD oscillator) indicating external day/night cycle is $\phi_{LD}$, a phase of the oscillator (group) (VL oscillator (group)) indicating VLSCN is $\phi_{VL}$, a phase of the oscillator (group) (DM oscillator (group)) indicating DMSCN is $\phi_{DM}$. The results of differentiation of $\phi_{LD}$, $\phi_{VL}$, and $\phi_{DM}$ are expressed by the following Expressions 1 to 3, respectively.

[Expression 1]

$$\frac{d\phi_{LD}}{dt} = \omega_{LD} \tag{1}$$

[Expression 2]

$$\frac{d\phi_{VL}}{dt} = \omega_{VL} + \kappa_{L \to V} f_1(\phi_{LD} - \phi_{VL}) + \kappa_{D \to V} f_2(\phi_{DM} - \phi_{VL}) + \xi_{VL}(t) \tag{2}$$

[Expression 3]

$$\frac{d\phi_{DM}}{dt} = \omega_{DM} + \kappa_{V \to D} f_3(\phi_{VL} - \phi_{DM}) + \xi_{DM}(t) \tag{3}$$

In Expressions 1 to 3, $\omega_h$ (h=LD, VL, and DM) is an angular velocity determined by the natural period ($T_h$) of the oscillator, and is expressed by $\omega_h = 2\pi/T_h$.

Also, $\kappa_s$ (s=L→V, D→V, V→D) is a parameter indicating the intensity of an entrainment function (function indicating mutual interaction of phases). The parameter $\kappa_{L \to V}$ in Expression 2 indicates the intensity of the action by the LD oscillator on the VL oscillator, and the parameter $\kappa_{D \to V}$ indicates the intensity of the action by the DM oscillator on the VL oscillator. The parameter $\kappa_{V \to D}$ of Expression 3 indicates the intensity of the action by the VL oscillator on the DM oscillator.

The function $f_i$ (i=1, 2, and 3) is an entrainment function. The function $\xi_h(t)$ (h=VL, DM) represents fluctuations of the clock-gene expressions of the individual neurons in VLSCN and DMSCN.

The cycle of the external day/night is exactly 25 hours, and thus it is possible to derive an exact solution of the phase of the LD oscillator from Expression 1 as shown by the following Expression 4.

[Expression 4]

$$\phi_{LD}(t) = \omega_{LD} t + \alpha \tag{4}$$

Here, $\alpha$ is an initial value (phase in an initial state). The jet-lag simulation is performed by mutation of $\alpha$ to $\alpha + \beta$, that is to say, by changing the phase of the LD oscillator by the amount of time difference $\beta$. In the simulation section 32, $\alpha$ is identified by time of the current position, and $\beta$ is identified by the time difference input by the user.

For example, by considering the following Expressions 5 to 7, it is possible to see the quality of the model.

[Expression 5]

$$\overline{\xi_{VL}}(t) = 0 \tag{5}$$

[Expression 6]

$$\kappa_{D \to V} \ll \kappa_{L \to V} \tag{6}$$

[Expression 7]

$$f_1(\phi_{LD}-\phi_{VL}) \equiv \phi_{LD}-\phi_{VL} \qquad (7)$$

Expression 5 indicates that fluctuations of the VL oscillator are disregarded by averaging. Expression 6 indicates that the intensity of information-propagation factor promoting synchronization from DMSCN to VLSCN is by far weaker than the intensity of entrainment of the VLSCN expression cycle to the external photoenvironment. As described above, if light irradiation time is suddenly changed, the expression cycle of the clock genes of VLSCN neurons is synchronized with the irradiation time in an early stage after the change. Expression 7 indicates simplification of an entrainment function from the external photoenvironment to a simplest form.

At this time, Expression 2 is expressed by the following Expression 8 in a simple form.

[Expression 8]

$$\frac{d\phi_{VL}}{dt} = \omega_{VL} + \kappa_{L \to D}(\phi_{LD} - \phi_{VL}) \qquad (8)$$

From Expression 8, the VL oscillator phase $\phi_{VL}(t)$ is expressed as the following Expression 9. The value α' in Expression 9 is expressed by the following Expression 10. Here, C is a predetermined coefficient.

[Expression 9]

$$\phi_{VL}(t) = \omega_{LD}t + \alpha + \frac{\omega_{VL} - \omega_{LD}}{\kappa_{L \to V}} + C\exp(-\kappa_{L \to V}t) \simeq \omega_{LD}t + \alpha'(t \to \infty) \qquad (9)$$

[Expression 10]

$$\alpha' \equiv \alpha + \frac{\omega_{VL} - \omega_{LD}}{\kappa_{L \to V}} \qquad (10)$$

Expression 9 indicates that the VL oscillator synchronizes immediately with the LD oscillator with a phase difference α'. The time for entrainment (until synchronization) is changed according to $\kappa_{L \to V}$, which indicates the intensity of operation of the LD oscillator toward the VL oscillator.

By the descriptions so far, it is understood that asymmetry in jet lag between a flight to the east and a flight to the west is caused by the function $f_3(\phi_{VL}-\phi_{DM})$ in Expression 3.

Thus, a parameter δ is introduced so as to break symmetry as shown in Expression 11 to determine the function $f_3(\phi_{VL}-\phi_{DM})$, and then it is possible to identify what is the value of the parameter δ that is best suited to indicate asymmetry of the jet lag.

[Expression 11]

$$f_3(\phi_{VL} - \phi_{DM}) \equiv \sin(\phi_{VL} - \phi_{DM}) + \frac{\delta}{6}\cos[2(\phi_{VL} - \phi_{DM})] \qquad (11)$$

As shown in the following Expression 12, it is possible to disregard fluctuations of the DM oscillator by averaging.

[Expression 12]

$$\overline{\xi_{DM}}(t)=0 \qquad (12)$$

In this example, Expression 3, which indicates differentiation of the phase of the DM oscillators, is expressed as the following Expression 13.

[Expression 13]

$$\frac{d\phi_{DM}}{dt} = \omega_{DM} + \kappa_{V \to D}\left[\sin(\phi_{VL} - \phi_{DM}) + \frac{\delta}{6}\cos[2(\phi_{VL} - \phi_{DM})]\right] \qquad (13)$$

When jet-lag simulation is performed in Japan, in general, many people suffer from slight jet lag (social jet lag) while still staying in Japan. The expression cycles of VLSCN and DMSCN are not fully in synchronism with an external sunshine cycle. Accordingly, when simulation is performed, in addition to Japan time α and a time difference β, it is necessary to measure and input biological time of a user to be simulated as initial values of phases of completely synchronized VL oscillator and DM oscillator. Initial states of $\phi_{VL}$ and $\phi_{DM}$ are identified on the basis of the input biological time.

In the simulation, Expression 14 to Expression 16, which have the above-described characteristics, are used.

[Expression 14]

$$\frac{d\phi_{LD}}{dt} = \omega_{LD} \Rightarrow \phi_{LD}(t) = \omega_{LD}t + \alpha + \beta \qquad (14)$$

[Expression 15]

$$\frac{d\phi_{VL}}{dt} = \omega_{VL} + \kappa_{L \to V}f_1(\phi_{LD} - \phi_{VL}) + \kappa_{D \to V}f_2(\phi_{DM} - \phi_{VL}) + \xi_{VL}(t) \qquad (15)$$

[Expression 16]

$$\frac{d\phi_{DM}}{dt} = \omega_{DM} + \kappa_{V \to D}f_3(\phi_{VL} - \phi_{DM}) + \xi_{DM}(t) \qquad (16)$$

It is thought that jet lag occurs while desynchronization occurs between the expression cycle of VLSCN and the expression cycle of DMSCN (the expression cycle of the clock genes of VLSCN neurons and the expression cycle of the clock genes of DMSCN neurons). By performing simulation on changes of phases of the VL oscillator and the DM oscillator on the basis of Expression 14 to Expression 16, and to identify time during which phases of the VL oscillator and the DM oscillator are out of synchronization with each other, it becomes possible to identify a time period during which the jet lag occurs and time until the jet lag is cured, etc.

In this regard, when simulation is tried in a system including the VL oscillator group and the DM oscillator group, the following Expressions 17 to 19 are used by expanding Expressions 14 to 16.

[Expression 17]

$$\frac{d\phi_{LD}}{dt} = \omega_{LD} \Rightarrow \phi_{LD}(t) = \omega_{LD}t + \alpha + \beta \qquad (17)$$

[Expression 18]

$$\frac{d\phi_{VL,i}}{dt} = \omega_{VL,i} + \kappa_{L \to V}f_1(\phi_{LD} - \phi_{VL}) + \kappa_{D \to V}\sum_j f_2(\phi_{DM,j} - \phi_{VL,i}) + \kappa_{V \leftrightarrow V}\sum_{j(j \neq i)} f_4(\phi_{VL,j} - \phi_{VL,i}) + \xi_{VL,i}(t) \qquad (18)$$

[Expression 19]

$$\frac{d\phi_{DM,i}}{dt} = \omega_{DM,i} + \kappa_{V \to D}\sum_j f_3(\phi_{VL,j} - \phi_{DM,i}) + \kappa_{D \leftrightarrow D}\sum_{j(j \neq i)} f'_4(\phi_{DM,j} - \phi_{DM,i}) + \xi_{DM,j}(t) \qquad (19)$$

The above-described mathematical model information is stored in the model-information storage section 33 as model information, and is used for the jet-lag simulation.

FIG. 7 is a schematic diagram illustrating a change in phase of each oscillator.

A circle shown in FIG. 7 denotes a clock having one around of 24 hours. A tinted circular mark $o_{LD}$ on an outer circle denotes an LD oscillator. Also, a shaded circular mark $o_{VL}$ on an inner circle denotes a VL oscillator (group), and a circular mark o$_{DM}$ denotes a DM oscillator (group).

The LD oscillator moves on the outer circle, and the VL oscillator and the DM oscillator move on the inner circle counterclockwise in the direction of an arrow individually at angular velocity of ω$_h$. For example, the LD oscillator goes around the outer circle in substantially 24 hours. When jet lag does not occur, the VL oscillator and the DM oscillator move so as to follow the LD oscillator. In the following, a description will be given on the assumption that a counterclockwise direction is a forward direction, and a clockwise direction is the opposite direction.

A position of the LD oscillator at the time of starting simulation is identified by the user's current position and time. Also, a position of VL at the time of starting simulation is identified by the user's biological time. The positions of the VL oscillator and the DM oscillator, shown in FIG. 7, indicate what time it is by the user's biological time.

When simulation is started assuming a flight to the east, as shown in FIG. 8, the position of the LD oscillator is set such that that position is moved in the forward direction by the amount of time difference input by the user.

In the example in FIG. 8, the position of the LD oscillator is moved from the point P$_1$ to the point P$_2$ in the forward direction. A distance from the position P$_1$ to the position P$_2$ on the outer arc is substantially ¼ one round, and thus FIG. 8 shows a state at the time of starting simulation in the case of inputting advance of 6 hours as a time difference. As shown by a bi-directional arrow, the intensity of entrainment operated between the LD oscillator and the VL oscillator at this time is expressed by $\kappa_{L \to V} f_1(\phi_{LD}-\phi_{VL})$ in Expression 15.

Figure 9:
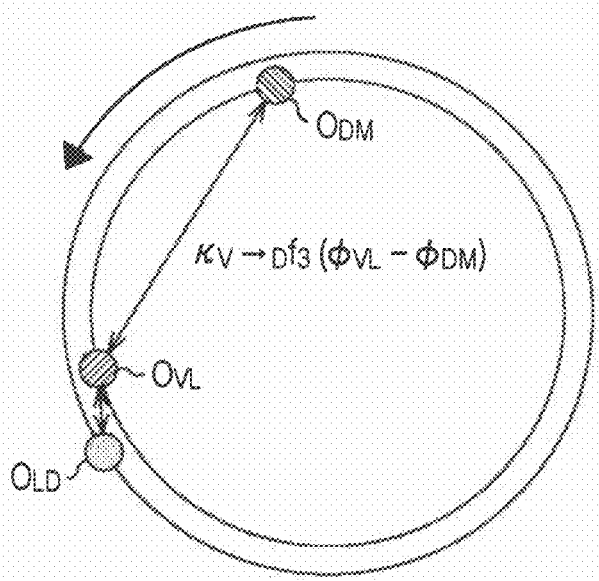
FIG. 9 is a diagram continued from FIG. 8 illustrating an example of simulation.

FIG. 9 is a diagram illustrating a state of each oscillator after a predetermined period of time has passed from time when the position of the LD oscillator is set as shown in FIG. 8.

As shown in FIG. 9, the VL oscillator quickly follows the LD oscillator, whereas the DM oscillator does not follow the LD oscillator soon. The state shown in FIG. 9 is a state in which desynchronization occurs between VLSCN and DMSCN. In this state, jet lag occurs. As shown by the bi-directional arrow in FIG. 9, the intensity of entrainment operated between the VL oscillator and the DM oscillator at this time is expressed by $\kappa_{V \to D} f_3(\phi_{VL}-\phi_{DM})$ in Expression 16.

Figure 10:
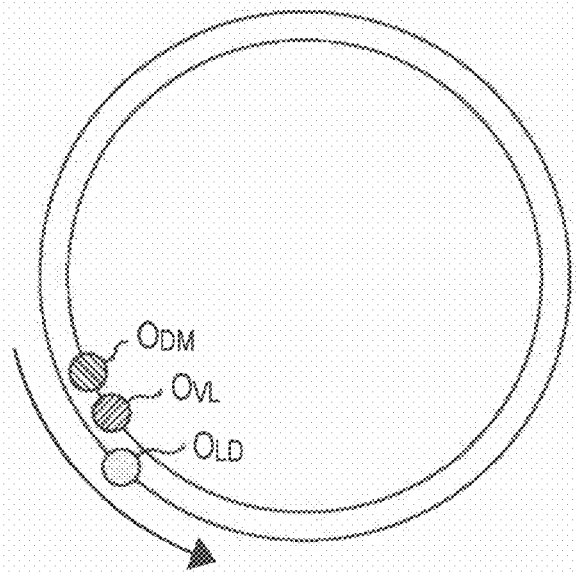
FIG. 10 is a diagram continued from FIG. 9 illustrating an example of simulation.

FIG. 10 is a diagram illustrating a state of each oscillator after a predetermined period of time has further passed from the state of FIG. 9.

As shown in FIG. 10, the VL oscillator and the DM oscillator are resynchronized after a predetermined time period has passed from time when desynchronization occurred. It is thought that jet lag occurs until the state shown in FIG. 10, and thus the time period from when the state in FIG. 9 to the state in FIG. 10 is presented to the user as the time during which jet lag occurs, for example.

Figure 11:
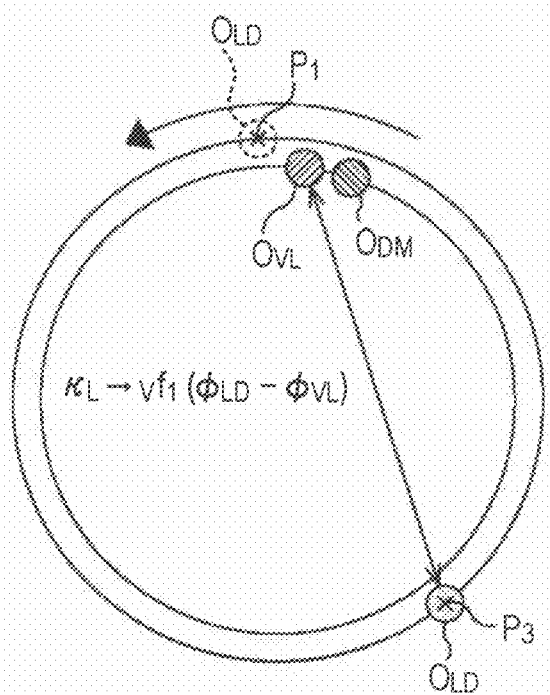
FIG. 11 is a diagram illustrating an example of simulation when time is delayed.

FIG. 11 is a diagram illustrating a state of each oscillator in the simulation assuming a flight to the west.

The simulation on the assumption of a flight to the west is carried out basically in the same manner as the simulation on the assumption of a flight to the east. That is to say, when simulation is started assuming a flight to the west, as shown in FIG. 11, the position of the LD oscillator is set such that that position is moved in the backward direction by the amount of time difference input by the user.

In the example in FIG. 11, the position of the LD oscillator is moved from the point P$_1$ to the point P$_3$ in the backward direction. As shown by a bi-directional arrow in FIG. 11, the intensity of entrainment operated between the LD oscillator and the VL oscillator at this time is expressed by $\kappa_{L \to V} f_1(\phi_{LD}-\phi_{VL})$ in Expression 15.

Figure 12:
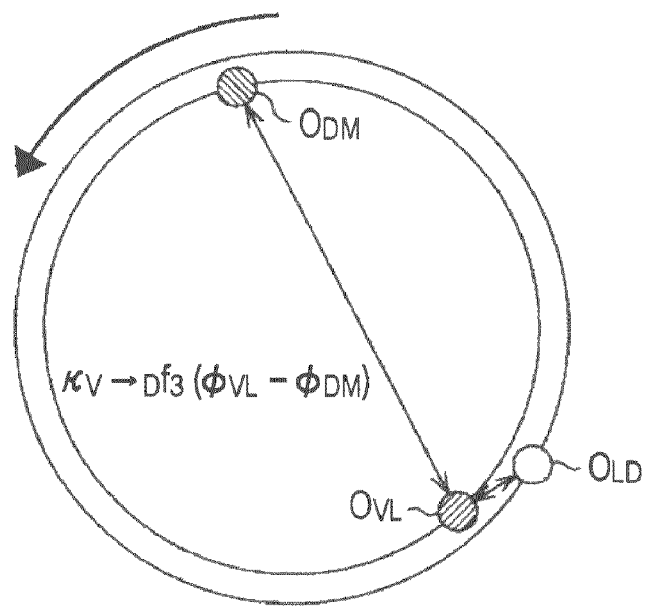
FIG. 12 is a diagram continued from FIG. 11 illustrating an example of simulation.

FIG. 12 is a diagram illustrating a state of each oscillator after a predetermined period of time has passed from time when the position of the LD oscillator is set as shown in FIG. 11.

As shown in FIG. 12, the VL oscillator quickly follows the LD oscillator, whereas the DM oscillator does not follow the LD oscillator soon. The state shown in FIG. 12 is a state in which desynchronization occurs between VLSCN and DMSCN. In this state, jet lag occurs. As shown by the arrow in FIG. 12, the intensity of entrainment operated between the VL oscillator and the DM oscillator at this time is expressed by $\kappa_{V \to D} f_3(\phi_{VL}-\phi_{DM})$ in Expression 16.

Figure 13:
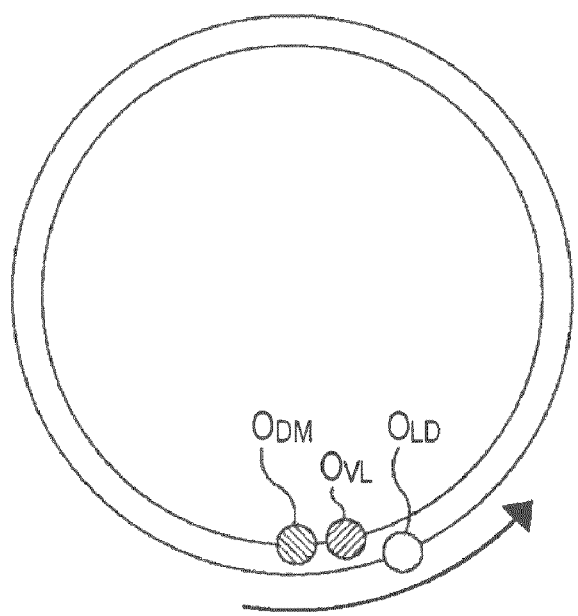
FIG. 13 is a diagram continued from FIG. 12 illustrating an example of simulation.

FIG. 13 is a diagram illustrating a state of each oscillator after a predetermined period of time has further passed from the state of FIG. 12.

As shown in FIG. 13, the VL oscillator and the DM oscillator are resynchronized after a predetermined time period has passed from time when desynchronization occurred. It is thought that jet lag occurs until the state shown in FIG. 13, and thus the time period from when the state in FIG. 12 to the state in FIG. 13 is presented to the user as the time during which jet lag occurs, for example.

The jet-lag simulation by the simulation section 32 is performed as described above. Images displaying the movement of each oscillator as shown from FIG. 7 to FIG. 13 may be displayed on the display as simulation results of the jet lag to be presented to the user.

Description of Programs

The above-described series of processing can be executed by hardware or by software. When the series of processing is executed by software, programs constituting the software may be installed in a computer built in a dedicated hardware. Alternatively, the programs may be installed in a general-purpose personal computer, etc.

The programs to be installed are provided by being recorded on a removable media 21, shown in FIG. 4, including an optical disc (a CD-ROM (Compact Disc-Read Only Memory), a DVD (Digital Versatile Disc), etc.,), a semiconductor memory, etc. Also, the programs may be provided through a wired or wireless medium, such as a local area network, the Internet, and digital broadcasting. The programs can be installed in the ROM 12 or the storage section 18 in advance.

In this regard, the programs executed by the computer may be programs that are processed in time series in accordance with the described sequence in this specification. Alternatively, the programs may be programs to be executed in parallel or at necessary timing, such as at the time of being called, or the like.

The present application contains subject matter related to that disclosed in Japanese Priority Patent Application JP 2010-109644 filed in the Japan Patent Office on May 11, 2010, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. An information processing apparatus comprising:
   an acquisition means for acquiring information on biological time of a user and information on a time difference between a movement source of the user and a movement destination;

a storage means for storing model information produced by modeling a sunshine pattern, an expression pattern of a clock gene of a neuron of a ventrolateral area of a suprachiasmatic nucleus, and an expression pattern of a clock gene of a neuron of a dorsomedial area; and when a sunshine pattern of the movement source is changed in accordance with the time difference so as to become a sunshine pattern of the movement destination of the user, a simulation means for simulating the expression pattern of the clock gene of the neuron of the ventrolateral area and the expression pattern of the clock gene of the neuron of the dorsomedial area on the basis of the model information using a state identified by the biological time of the user as a starting state.

2. The information processing apparatus according to claim 1, further comprising an output means for outputting information on a predicted jet-lag syndrome occurring on the user on the basis of a simulation result by the simulation means.

3. The information processing apparatus according to claim 2, wherein the output means displays a time period during which desynchronization occurs between the expression pattern of the clock gene of the neuron of the ventrolateral area and the expression pattern of the clock gene of the neuron of the dorsomedial area.

4. The information processing apparatus according to claim 2, wherein the output means displays an image indicating the expression pattern of the clock gene of the neuron of the ventrolateral area and the expression pattern of the clock gene of the neuron of the dorsomedial area from time when desynchronization occurs to time when re-synchronization is established.

5. A method of processing information, comprising the steps of:

acquiring information on biological time of a user and information on a time difference of a movement destination of the user; and when a sunshine pattern of a movement source of the user is changed in accordance with the time difference so as to become a sunshine pattern of the movement destination of the user, simulating an expression pattern of a clock gene of a neuron of a ventrolateral area of a suprachiasmatic nucleus and an expression pattern of a clock gene of a neuron of a dorsomedial area on the basis of model information stored in a storage means and produced by modeling a sunshine pattern, an expression pattern of a clock gene of a neuron of a ventrolateral area of the suprachiasmatic nucleus, and an expression pattern of a clock gene of a neuron of a dorsomedial area using a state identified by the biological time of the user as a starting state.

6. A program for causing a computer to perform processing comprising the steps of:

acquiring information on biological time of a user and information on a time difference of a movement destination of the user; and when a sunshine pattern of a movement source of the user is changed in accordance with the time difference so as to become a sunshine pattern of the movement destination of the user, simulating an expression pattern of a clock gene of a neuron of a ventrolateral area of a suprachiasmatic nucleus and an expression pattern of a clock gene of a neuron of a dorsomedial area on the basis of model information stored in a storage means and produced by modeling a sunshine pattern, an expression pattern of a clock gene of a neuron of a ventrolateral area of the suprachiasmatic nucleus, and an expression pattern of a clock gene of a neuron of a dorsomedial area using a state identified by the biological time of the user as a starting state.

7. An information processing apparatus comprising:

an acquisition mechanism acquiring information on biological time of a user and information on a time difference between a movement source of the user and a movement destination;

a storage mechanism storing model information produced by modeling a sunshine pattern, an expression pattern of a clock gene of a neuron of a ventrolateral area of a suprachiasmatic nucleus, and an expression pattern of a clock gene of a neuron of a dorsomedial area; and when a sunshine pattern of the movement source is changed in accordance with the time difference so as to become a sunshine pattern of the movement destination of the user, a simulation mechanism simulating the expression pattern of the clock gene of the neuron of the ventrolateral area and the expression pattern of the clock gene of the neuron of the dorsomedial area on the basis of the model information using a state identified by the biological time of the user as a starting state.

* * * * *